(12) United States Patent
Reinhardt et al.

(10) Patent No.: US 9,316,626 B2
(45) Date of Patent: Apr. 19, 2016

(54) METHOD AND DEVICE FOR DIAGNOSING ELECTRODES IN SENSOR ELEMENTS

(75) Inventors: Goetz Reinhardt, Boeblingen (DE); Torsten Handler, Stuttgart (DE); Jens Wagner, Stuttgart (DE); Lothar Diehl, Gemmrigheim (DE); Bjoern Alexander Schuetz, Besigheim (DE); Helge Schichlein, Stuttgart (DE); Thomas Seiler, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 273 days.

(21) Appl. No.: 14/000,812

(22) PCT Filed: Dec. 28, 2011

(86) PCT No.: PCT/EP2011/074153
§ 371 (c)(1),
(2), (4) Date: Oct. 16, 2013

(87) PCT Pub. No.: WO2012/113481
PCT Pub. Date: Aug. 30, 2012

(65) Prior Publication Data
US 2014/0033794 A1 Feb. 6, 2014

(30) Foreign Application Priority Data

Feb. 22, 2011 (DE) .......................... 10 2011 004 520

(51) Int. Cl.
*G01N 33/00* (2006.01)
*G01N 27/406* (2006.01)
*G01N 27/407* (2006.01)

(52) U.S. Cl.
CPC .......... *G01N 33/0006* (2013.01); *G01N 27/407* (2013.01); *G01N 27/4065* (2013.01); *G01N 33/007* (2013.01)

(58) Field of Classification Search
CPC ............ G01N 27/4175; G01N 27/419; G01N 33/007; G01N 27/407; G01N 33/0006; F02D 41/1495; Y02T 10/47
USPC ......................................................... 73/1.06
See application file for complete search history.

(56) References Cited

U.S. PATENT DOCUMENTS 5,558,752 A * 9/1996 Wang .................... G01N 27/419
123/672
5,804,700 A * 9/1998 Kwon ................ G01N 27/4175
204/401

(Continued)

FOREIGN PATENT DOCUMENTS

DE      29 46 440      5/1981
DE      441 00 16      9/1994

(Continued)

OTHER PUBLICATIONS

Robert Bosch GmbH : "Sensoren im Kraftfahrzeug " [Sensors in Motor Vehicles], 2007 edition, pp. 154-159.

*Primary Examiner* — Freddie Kirkland, III
(74) *Attorney, Agent, or Firm* — Kenyon & Kenyon LLP

(57) ABSTRACT

A method for diagnosing a sensor element for detecting at least one fraction of a gas component of a gas in a measuring gas chamber, in particular a sensor element for detecting oxygen in an exhaust gas of an internal combustion engine. The sensor element includes at least one first electrode, to which the gas may be applied, and at least one second electrode, the first electrode and the second electrode being connected via at least one solid electrolyte. A diagnostic signal is applied between the first electrode and the second electrode, a response signal being detected between the first electrode and the second electrode.

14 Claims, 2 Drawing Sheets

(56) References Cited

U.S. PATENT DOCUMENTS

| | | | |
|---|---|---|---|
| 6,059,947 A | 5/2000 | Kato et al. | |
| 6,266,993 B1 * | 7/2001 | Diehl | G01N 27/4175 204/427 |
| 6,290,829 B1 * | 9/2001 | Kato | G01N 27/4074 204/401 |
| 6,551,499 B1 | 4/2003 | Springhorn et al. | |
| 6,554,983 B2 * | 4/2003 | Imamura | G01N 27/419 204/425 |
| 6,645,367 B1 * | 11/2003 | Zhang | G01N 27/4175 204/425 |
| 7,779,669 B2 * | 8/2010 | Fukagai | F02D 41/1456 701/31.3 |
| 7,799,203 B2 * | 9/2010 | Ieda | G01N 27/4065 204/401 |
| 7,938,944 B2 * | 5/2011 | Suzuki | G01N 33/0037 204/401 |

FOREIGN PATENT DOCUMENTS

| | | |
|---|---|---|
| DE | 101 63 912 | 2/2003 |
| DE | 102 16 724 | 10/2003 |
| DE | 10 2008 043124 | 4/2010 |

* cited by examiner

METHOD AND DEVICE FOR DIAGNOSING ELECTRODES IN SENSOR ELEMENTS

FIELD OF THE INVENTION

The present invention relates to a method for diagnosing a sensor element for detecting at least one fraction of a gas component of a gas in a measuring gas chamber.

BACKGROUND INFORMATION

Devices and methods for detecting at least one fraction of a gas component of a gas in a measuring gas chamber are believed to be understood from the related art. For example, the gas may be an exhaust gas of an internal combustion engine, in particular in the automotive field, and the measuring gas chamber may be an exhaust system, for example. The device may be a lambda sensor in this case, for example.

Such lambda sensors are discussed, for example, in Robert Bosch GmbH: Sensoren im Kraftfahrzeug (Sensors in Motor Vehicles), 2007 edition, pages 154-159. Lambda sensors, in particular universal lambda sensors, set two substance flows, in particular oxygen flows, in equilibrium between a cavity of the device and the measuring gas chamber. One of the substance flows is driven in this case by concentration differences via a diffusion barrier. A further substance flow is driven via a solid electrolyte and two electrodes, in particular two pump electrodes, controlled by an applied pump current. The pump current may be regulated in such a way that a constant and very low oxygen concentration results in the cavity. A concentration profile via the diffusion barrier is unambiguously determined by a constant regulating point in the cavity, in particular a constant setpoint voltage resulting in an oxygen concentration, and by an exhaust-side oxygen concentration. An inflow of oxygen molecules from the measuring gas chamber to the cavity results in accordance with this unambiguous concentration profile and corresponds to the regulated pump current. This pump current may therefore be a measured value for the oxygen concentration in the measuring gas chamber, in particular for the oxygen concentration applied on the exhaust side.

In particular two different variants of lambda sensors are believed to be understood from the related art: lambda sensors having two cells and lambda sensors having only one cell.

Lambda sensors having two cells are discussed, for example, in DE 4410016 C2. An oxygen detection device is discussed therein for detecting an oxygen concentration of a measuring gas, including a first electrochemical cell having a reference electrode and having a measuring electrode, and a second electrochemical cell having an electrode pair.

In such sensors having two cells, the first electrochemical cell is usually integrated as a measuring cell with electrodes in a cavity and on a reference gas chamber having a defined, mostly higher oxygen concentration. This measuring cell typically displays a resulting Nernst voltage characteristic, which is distinguished by a sharp potential increase as soon as the oxygen concentration in the cavity sinks to zero. A pump current is regulated to a regulated setpoint value, so that a corresponding potential results within the potential increase at the measuring cell. The regulating setpoint value typically includes a Nernst voltage of 450 mV, which is used for the purpose of regulating an oxygen concentration in the cavity of $\lambda=1$. This regulating setpoint value is typically 450 mV over the entire service life of the lambda sensor. If the regulating setpoint value of the measuring cell changes within the sharp potential increase, for example, to 300 mV-600 mV, the oxygen concentration in the measuring chamber does not decisively change. The oxygen inflow and the pump current are thus hardly influenced.

Lambda sensors having only one cell are discussed, for example, in DE 2946440 A1. A method for obtaining a control variable for regulating the air-fuel ratio of the operating mixture of internal combustion engines with the aid of an exhaust gas measuring sensor exposed to the exhaust gas flow is provided in this unexamined published application.

In lambda sensors having only one cell, an outer electrode of the one cell, in particular a pump cell, is typically applied to a gas chamber having a high oxygen concentration, for example, to a reference volume. A fixed voltage is applied between the outer electrode and an inner electrode of the pump cell. As soon as an oxygen concentration in a cavity is close to 0, a potential, in particular a Nernst potential, increases strongly and partially compensates for the applied voltage. A constant oxygen concentration in the cavity may thus also be regulated in this way with good precision. For this purpose, the voltage at the pump cell must exceed an ohmic voltage drop of a pump current via a resistor of the pump cell. A sum of the ohmic voltage drop and the desired Nernst potential, which may typically be 450 mV, is ideally applied. The voltage should actually be somewhat higher to compensate for contact resistances at the electrodes.

As in the case of lambda sensors having two cells, a change of the voltage at the strong potential increase, for example, in the case of Nernst voltages between 300 mV and 600 mV, i.e., a change of the voltage by +/−150 mV to the typical value of 450 mV, does not result in any substantial change of the oxygen concentration in the cavity. An oxygen inflow from the measuring gas chamber via a diffusion barrier and the pump current are typically hardly influenced by voltage changes.

Due to a strongly varying oxygen concentration in the exhaust gas, the resulting pump current may be subjected to strong variations, the voltage being tracked in order to compensate for the changed ohmic voltage drop.

Lambda sensors, for example, broadband lambda sensors, are used in particular in the exhaust flow direction downstream from a $NO_x$ storage catalytic converter (NSC), in order to diagnose the NSC. A time is typically ascertained for this purpose using the lambda sensor, which elapses until a rich jump in a mixture formation breaks through the NSC, i.e., until the lambda sensor indicates a specific rich pump current.

A method for operating a broadband lambda sensor is discussed in patent specification DE 10216724 C1, in order to also maintain the measuring sensitivity of a sensor in the case of fuel post-injection during lean operation and/or in a "fast light off." During the duration of a fuel post-injection and/or the "fast light off," a pump voltage is repeatedly reversed in polarity, so that an anodic pump current briefly results, which pumps oxygen ions into a measuring chamber, which oxidize hydrocarbons therein.

It is understood to be legally required that the function of a lambda sensor be diagnosed and monitored over its lifetime, for example, to diagnose an NSC in a vehicle. It is understood that the characteristic of lambda sensors may change over longer operating times. For example, the relationship between an applied oxygen concentration in the exhaust gas and a resulting pump current of the sensor element changes. If the characteristic changes due to aging effects in the diffusion barrier, for example, due to a change in the material or clogging, the slope of the characteristic changes in particular. The fundamental curve profile is maintained, however. Such changes may be compensated for in principle by a compensation at a known measuring point, for example, in the case of operation using ambient air.

A gas sensor and a method for the operation thereof are discussed in DE 10163912 A1, in the case of which operating phases occur, during which the measuring gas, which communicates with a diffusion chamber of the gas sensor, corresponds to a reference gas and accordingly a λ value of the measuring gas is known at this point in time. These operating phases having a known λ value may be used according to this publication for the regular monitoring or calibration of measuring signals of the gas sensor. It may be provided for this purpose that the pump voltage to be applied to the pump electrodes of a pump cell is reversed in polarity in relation to a normal pump operation periodically and/or in predefined operating phases, so that polarization effects in a ceramic body are dissipated and changes of sensor signals connected thereto are prevented.

A forced pump current reversal for regenerating the pumping capability is discussed in both DE 10216724 C1 and DE 10163912 A1.

In addition to aging effects in diffusion barriers, the activity of the electrodes may also decrease, for example, by contamination due to additives in oil and fuel, for example, silicon and/or lead. For example, an applied pump voltage may then no longer be sufficient in the event of high oxygen concentrations in the exhaust gas, in order to apply a required pump current. The characteristic thus flattens out strongly in particular in the case of high oxygen concentrations. Such a change of the characteristic may no longer be compensated for. In the case of a lambda sensor having two cells, this effect could be recognized by monitoring the regulated regulating point, in particular the setpoint voltage, as soon as the maximum possible setpoint voltage is no longer sufficient. Since such aging effects slowly increase, a decisive signal corruption may thus already occur earlier. Since the sensor element is not exposed to rich or lean gases at a position downstream from the NSC, except during a diagnosis of the NSC, but rather is continuously located in a λ=1 atmosphere, a pump capability of the sensor element may not be tested. A method is needed for checking the functional reliability, in particular of a pump cell, in the case of λ=1 atmosphere. Known methods for diagnosing a sensor element, for example, the above-described conventional monitoring of the sensor signal at a known measuring point, for example, in the case of application of ambient air, are greatly restricted, since less critical aging effects and production scatter may also have similar effects in this case.

SUMMARY OF THE INVENTION

The present invention is essentially described hereafter, without restriction of further possible embodiments, with reference to methods and devices which are used for the quantitative and/or qualitative detection of at least one gas component in a measuring gas chamber.

Therefore, a method and a device for diagnosing a sensor element for detecting at least one fraction of a gas component of a gas in a measuring gas chamber, in particular a sensor element for detecting oxygen in an exhaust gas of an internal combustion engine are provided, which at least largely avoid the disadvantages of known methods and devices. The sensor element may be in particular a lambda sensor having at least one cell, which may have one cell or having two cells. The device, in particular the sensor element, includes at least one first electrode, to which a gas may be applied, and at least one second electrode. The first electrode and the second electrode are connected via at least one solid electrolyte. In a lambda sensor which may have one cell, the first electrode may be an inner electrode, for example. The second electrode may be an expansion electrode for this purpose. In a lambda sensor having two cells, the first electrode may also be an inner electrode, for example, and the second electrode may be an outer electrode, for example. The electrodes are manufactured from zirconium dioxide, for example. Furthermore, the device includes at least one controller, the controller being configured to carry out the method for diagnosing the sensor element, as described hereafter. A cell may be understood for this purpose to be an electrochemical measuring cell, which utilizes electrochemical properties, i.e., for example, a Nernst cell and/or a pump cell. The solid electrolyte may be configured as YSZ, ScSZ, and/or in the form of other types of solid electrolytes, for example. In this regard, reference may be made in principle to all known sensor elements, which are also usable in principle within the scope of the present invention. The controller may be connected via an interface to the sensor element, for example.

The controller may also be completely or partially integrated into the sensor element, however. The controller may, however, also be entirely or partially integrated into other components, for example, in a plug and/or in an engine controller, for example. The controller may include at least one application device, for example, to apply current and/or voltage to the electrodes. The application device may be a voltage source and/or a current source, for example. Furthermore, the controller may optionally include a measuring device, for example, a voltage measuring device and/or a current measuring device. Furthermore, the controller may optionally include an analysis device, for example, a data processing device, for example. Furthermore, the controller may optionally include at least one signal generator. The controller may additionally optionally include at least one regulator, for example, at least one lock-in regulator. The sensor element may include at least one cavity, to which gas from the measuring gas chamber may be applied, in particular via a diffusion barrier. The first electrode may be at least partially connected to the cavity, the cavity being connected to the measuring gas chamber, in particular via a diffusion barrier. The second electrode may be at least partially connected to the measuring gas chamber.

In the provided method for diagnosing the sensor element for detecting at least one fraction of a gas component of a gas in a measuring gas chamber, as described above, a diagnostic signal is applied between the first electrode and the second electrode. A response signal is detected between the first electrode and the second electrode. "First" and "second" are used as designations for this purpose, without indicating that possibly still further electrodes may exist and without indicating a sequence. The detection of the response signal may take place at the same time or also offset in time, for example, intermittently, with the application of the diagnostic signal. The diagnostic signal may be in particular a constant diagnostic signal. For example, the diagnostic signal may also be a chronologically continuously varying diagnostic signal. The diagnostic signal may be, for example, an electric current and/or an electric voltage, the electric current being applied, for example, in such a way that it flows through a cell including the first electrode and the second electrode, and/or the voltage being applied, for example, to a cell including the first electrode and the second electrode.

In particular, the diagnostic signal may be a continuously varying signal, for example, a periodic signal, for example, selected from the following group of periodic signals: a sinusoidal signal; a rectangular signal; a triangular signal; a sawtooth signal; a stepped signal; and a pulsed signal. For example, a constant signal or a signal which increases or decreases in steps may particularly be used. The frequency of a periodic diagnostic signal may be constant or may vary chronologically. In principle, the signal may also be combinations of the mentioned pulse shapes or pulse shapes which are not mentioned here. The response signal may be in particular an electric current and/or a voltage, particularly which may be a time curve of an electric current and/or a time curve of a voltage. The response signal may in particular be detected chronologically continuously, in particular as a function of time.

In the provided method, the diagnostic signal may be selected in particular from a voltage sequence and a current sequence. A sequence is understood to be a continuous or also discontinuous succession of signals, as described above. In particular, the voltage sequence and/or the current sequence may include a stepped sequence. Other signal shapes are described as examples hereafter.

In the method for diagnosing a sensor element, the diagnostic signal may be regulated to a setpoint sequence, for example, to a current sequence, in particular to a setpoint voltage sequence, particularly which may be to a Nernst voltage, between the first electrode and a reference electrode. The reference electrode may be at least partially connected to a reference gas chamber. The reference gas chamber may be connected in particular via the solid electrolyte to the cavity. The regulation of the diagnostic signal to a setpoint sequence, in particular to a constant Nernst voltage, may be used in particular for the purpose of setting an oxygen concentration in the cavity in a controlled way. The regulation of the diagnostic signal and the generation of the setpoint sequence and the detection of the response signal may be carried out with the aid of the controller.

The diagnostic signal and/or the setpoint sequence may include a variable, which may be a physical variable, in particular a voltage and/or an electric current. The diagnostic signal and/or the setpoint sequence may be varied in discrete steps, for example, in steps of 250 mV, in particular in steps of 150 mV, particularly which may be in steps of 25 mV starting from a predefined regulating point. The predefined regulating point may be a Nernst voltage between 20 mV and 650 mV, which may be a Nernst voltage between 250 mV and 550 mV, and particularly which may be a Nernst voltage of 450 mV, for example. The diagnostic signal and/or the setpoint sequence may be varied from the predefined regulating point toward higher and/or lower values.

The diagnostic signal and/or the setpoint sequence may include a variable which has at least one constant value. The variable may be, for example, a voltage and/or an electric current, for example, a Nernst voltage of 20-180 mV, which may be 50-150 mV, particularly may be 100 mV. In principle, the setpoint sequence may also have periodic signal shapes, as described above for the diagnostic signal.

The diagnostic signal and/or the setpoint sequence may include a variable which is chronologically continuously varied, for example, selected from the following group of signal shapes: a periodic signal; a sinusoidal signal; a rectangular signal; a triangular signal; a sawtooth signal; a stepped signal; and a pulsed signal. Particularly, it may be a constant signal or a signal which increases or decreases in steps. Combinations of the mentioned signal shapes and signal shapes which were not mentioned may also be used in principle.

A temperature of the sensor element may be regulated in particular. For example, the temperature may be kept at a constant value or increased or decreased. The regulation of this temperature may extend to the entire sensor element, for example. However, a defined temperature may also be applied to only parts of the sensor element.

The response signal may be compared in particular to at least one threshold value. This may relate to a current sequence, for example. The threshold value may include one or multiple comparison values and the diagnosis may be carried out as a function of the comparison, for example. For example, the response signal may also be compared to at least one threshold value as a function of the diagnostic signal, in particular the current sequence as a function of the voltage sequence, which is also to include the option of a comparison to at least one threshold value function. The threshold value may be constant, but may also vary, as a function of the response signal, in particular as a function of the signal shape and/or the dimension of the response signal. The threshold value may include a comparison curve, for example, having a tolerance band, and/or a tolerance value, for example. For example, in this way an aging state may be inferred, for example, if the response signal exceeds, falls below, or reaches the at least one threshold value.

Various options for the design of a threshold value condition are believed to be understood in principle to those skilled in the art. In particular, for example, an aging state of at least one of the electrodes and/or one or multiple diffusion barriers may be inferred by the comparison to at least one threshold value, in particular at least one threshold value function. The response signal, for example, an electric current, may have a relative change, for example, in relation to an electric current during normal operation. The relative change may be compared, for example, to a sensor-typical threshold value, for example, a sensor-typical limiting value. Normal operation may be understood for this purpose to be an operation, for example, which is regulated during the measuring operation, i.e., for example, in an operating mode which does not correspond to the diagnostic mode. The Nernst voltage may typically be 450 mV during normal operation.

In the method for diagnosing a sensor element, for example, the concentration of a fraction of a gas, for example, oxygen, in the exhaust gas may be varied. The method may be carried out at a fixed fraction of the gas or also at a varying fraction of the gas or also repeatedly at different fractions of the gas. The method may be carried out in the case of an air ratio $\lambda=1$, for example, however also in the case of $\lambda>1$ or $\lambda<1$.

For example, a reduced electrode activity for sensor elements having one cell or two cells may be recognized early and critical aging effects may be monitored by the provided method and the provided device.

Exemplary embodiments of the present invention are illustrated in the figures and will be explained in greater detail in the following description.

DETAILED DESCRIPTION

Figure 1A:
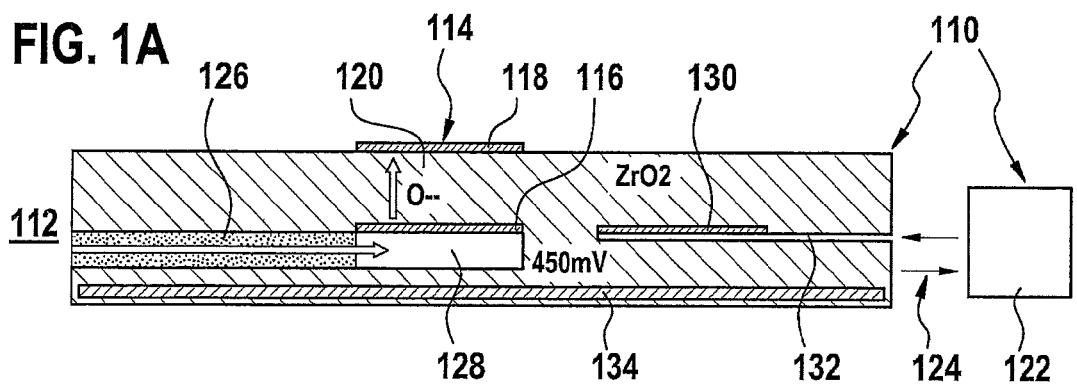
FIG. 1A shows an exemplary embodiment of a device according to the present invention having two cells.

FIG. 1A shows one exemplary embodiment of a device 110 according to the present invention for detecting at least one fraction of a gas component of a gas in a measuring gas chamber 112. Device 110 includes at least one sensor element 114. Sensor element 114 includes at least one first electrode 116, to which the gas may be applied, and at least one second electrode 118. First electrode 116 and second electrode 118 are connected via at least one solid electrolyte 120. Furthermore, device 110 includes at least one controller 122, for example, a data processing device, for example, a controller 122, which may be connected via an interface 124 to the sensor element 114. Device 110, in particular controller 122, is configured to carry out a method according to the present invention.

Sensor element 114 may include at least one cavity 128, to which gas from measuring gas chamber 112 may be applied, in particular via a diffusion barrier 126. First electrode 116 may be at least partially connected to cavity 128. Cavity 128 may be connected in particular via solid electrolyte 120 to measuring gas chamber 112, second electrode 118 being able to be at least partially connected to measuring gas chamber 112. In particular, in this case it may be a sensor element 114 having two cells, device 110 according to the present invention furthermore being able to include a reference electrode 130. Reference electrode 130 may be at least partially connected to a reference gas chamber 132. Reference gas chamber 132 may be connected to cavity 128 in particular via solid electrolyte 120. Sensor element 114 may furthermore include a heating element 134.

Figure 1B:
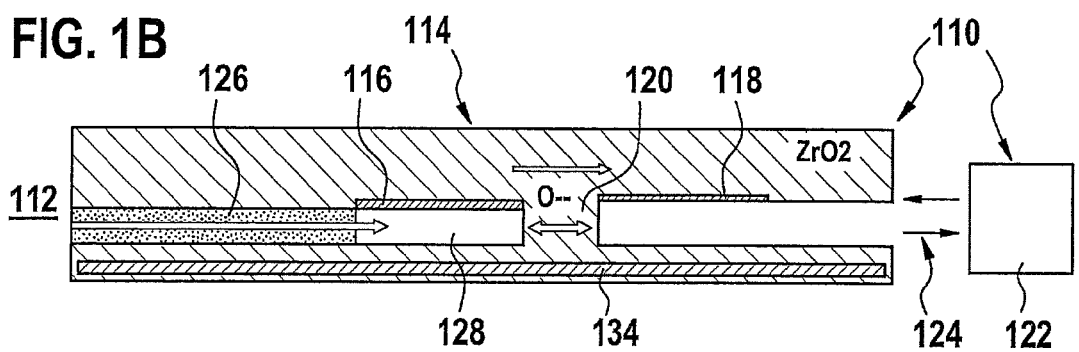
FIG. 1B shows an exemplary embodiment of a device according to the present invention having one cell.

According to the present invention, FIG. 1B shows another exemplary embodiment of a device 110 having one cell. Device 110 of this exemplary embodiment is essentially constructed like device 110 in FIG. 1A. However, this sensor element 114 does not include a reference electrode 130. Second electrode 118 may additionally be at least partially connected not to a measuring gas chamber 112, but rather to a reference gas chamber 132, to which a high oxygen concentration may be applied, for example. First electrode 116 may be configured in this exemplary embodiment in particular as an inner electrode and second electrode 118 may be configured in particular as an expansion electrode.

In addition to the specific embodiments of devices 110 shown in FIG. 1A and FIG. 1B, according to the present invention, devices 110 may be used in the method according to the present invention, which are configured at least partially corresponding to known devices 110, as described above in the related art.

Figure 2A:
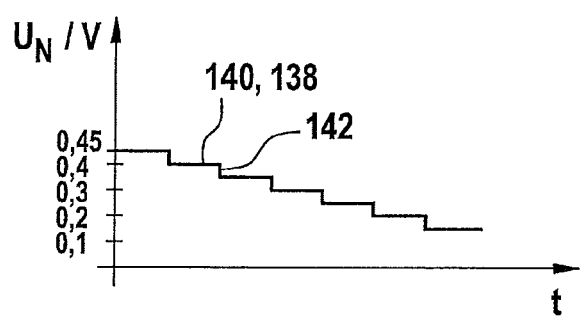
FIGS. 2A, 2B, 2C, and 2D show a method according to the present invention having a diagnostic signal increasing in steps.
Figure 2B:
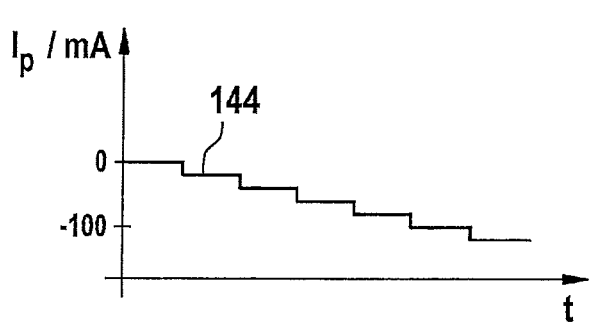
Figure 2C:
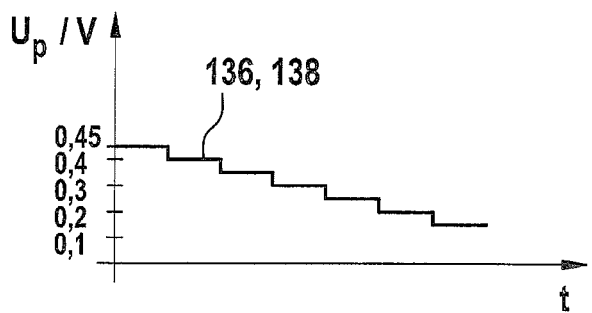
Figure 2D:
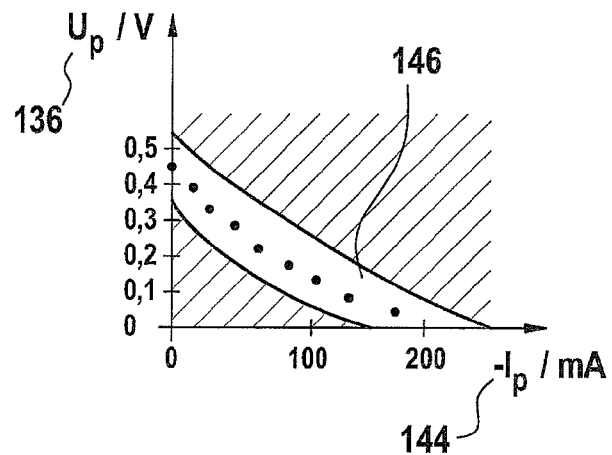

One exemplary embodiment of a method for diagnosing a sensor element 114 is shown in FIGS. 2A, 2B, 2C, and 2D. For example, a device 110 as described above and shown in FIGS. 1A and 1B may be used to execute this method. In this exemplary embodiment, a device 110 having two cells, as shown in FIG. 1A and described above, may be used. In principle, however, a device 110 having one cell, as shown in FIG. 1B, may also be used. A diagnostic signal 136, which is shown in FIG. 2D, is applied between first electrode 116 and second electrode 118.

Diagnostic signal 136 is shown in FIG. 2C, a pump voltage $U_p$ in volts being plotted over a time t. Diagnostic signal 136 may be selected in principle from a voltage sequence 138 and a current sequence. In this exemplary embodiment, diagnostic signal 136 is a voltage signal 138, in particular a voltage signal 138 increasing in steps.

Diagnostic signal 136 is regulated for this purpose to a setpoint sequence 140, in particular a voltage sequence 138, between first electrode 116 and reference electrode 130. Setpoint sequence 140 is shown in FIG. 2A as Nernst voltage $U_N$ in volts as a function of time t. Setpoint sequence 140 includes in this exemplary embodiment a variable, in particular a voltage, particularly which may be a Nernst voltage, which is varied in discrete or continuous steps 142, in particular decreasing in steps. Setpoint sequence 140, in particular the Nernst voltage between first electrode 116 and reference electrode 130, may be decreased in steps 142 of up to 250 mV, in particular in steps 142 of up to 150 mV, particularly in steps 142 of up to 25 mV may start from a predefined regulating point, for example, a Nernst voltage between 20 mV and 650 mV, which may be between 250 mV and 550 mV, and particularly which may be from 450 mV to 50 mV, for example. A high oxygen partial pressure is thus requested in cavity 128.

During each of these steps 142, oxygen ions are pumped from second electrode 118, in particular an outer electrode, to first electrode 116, in particular an inner electrode. The oxygen ions originate from the water decomposition at second electrode 118. This corresponds, for example, to a pump status of sensor element 114, as prevails in the case of a lean exhaust gas mixture during normal operation, which is distinguished by negative pump currents. During the method, a response signal 144 between first electrode 116 and second electrode 118 is detected, as shown in FIG. 2B as pump current $I_p$ in milliamperes as a function of time t.

A temperature of sensor element 114 may be regulated in a defined way. The method may advantageously be carried out in an operating state in which the heating power of heating element 134 of sensor element 114 and/or the temperature of a pump cell, including first electrode 116 and second electrode 118, are defined. Without defined regulation of the temperature, variations thereof may result in variations in the pump voltage. It is optionally advantageous for signal precision to carry out the method at decreased or increased heating power, in comparison to normal operation. Response signal 144 may be compared to a threshold value as a function of diagnostic signal 136. In FIG. 2D, diagnostic signal 136, in particular pump voltage $U_p$ in volts, is shown as a function of response signal 144, in particular negative pump current $-I_p$ in milliamperes. A tolerance band 146 is outlined, using which the ratios from diagnostic signal 136 may be compared to response signal 144 for steps 142.

For example, if the values of the ratios are within tolerance band 146, a piece of diagnostic information, for example, "operating correctly" and/or another piece of diagnostic information, which indicates that sensor element 114 is operating correctly, may be output. If at least one point, and/or multiple points and/or precisely one point lie or lies outside tolerance band 146, for example, a piece of diagnostic information "not operating correctly" and/or another piece of diagnostic information, which signals that sensor element 114 is not operating correctly, may be output. A piece of diagnostic information may be output on a screen and/or a display and/or acoustically, for example, with the aid of the regulation.

During each step, the ratio between the pump current and the required pump voltage between first electrode 116 and a second electrode 118 is evaluated. The resulting curve, for example, in the relevant current range, is to be within predefined tolerance band 146, so that the sensor is diagnosed as "operating correctly." An inactive second electrode 118 and/or first electrode 116 would result in impermissibly high pump voltages at a defined pump current, for example. For each sensor element 114, a $U_p$ to $I_p$ curve may be detected in the new state and stored in controller 122, for example, in particular in the control unit software. Therefore, for example, relevant tolerance band 146 for sensor elements 114 may be adapted during operation, in particular for aged sensor elements 114, to this measurement in the new state with respect to a scattering and/or an offset.

For example, the concentration of oxygen in the exhaust gas may be varied. The method may be carried out at λ=1. For example, it may be advantageous not to carry out the diagnosis at λ=1, but rather at other gas concentrations, in particular concentrations of oxygen. For this purpose, to judge an aging state, instead of an absolute pump voltage and/or an absolute pump current, a deviation from the normal pump current or the normal pump voltage may be used, in the case of a regulation to a Nernst voltage of 450 mV, for example.

Instead of a variation of setpoint sequence 140 in discrete steps 142, a setpoint sequence 140 may also be used, for example, which includes a variable, in particular a voltage, which has at least one constant value, which may be precisely one constant value, for example, a Nernst voltage between 600 mV and 50 mV, which may be between 300 mV and 75 mV, particularly which may be a Nernst voltage of 100 mV. If precisely one constant value is used, it may be checked whether the ratio of pump voltage to pump current is within tolerance band 146 in the case of this diagnostic signal 136, in particular this Nernst voltage.

Due to a characteristic, according to which the Nernst voltage at λ=1 changes very strongly in the event of changes of the oxygen concentration, a defined pump current may not be intentionally induced by a change of the Nernst voltage. In different structurally identical sensor elements 114 and during the service life of a sensor element 114, large differences in the resulting pump current are to be expected. A measurement of a broader pump voltage range may therefore ensure that a measuring point which may be evaluated may be detected in any case.

For example, a diagnostic signal 136 may also be applied, in particular a Nernst voltage which may be greater than a Nernst voltage during normal operation, for example, a Nernst voltage between 450 mV and 800 mV, which may be a Nernst voltage between 500 mV and 700 mV, particularly which may be a Nernst voltage of 600 mV. A positive pump current results therefrom, which corresponds to a lean operating state during normal operation. In this way, for example, in contrast to a diagnostic signal 136 which has a Nernst voltage less than a Nernst voltage during normal operation, an oxygen incorporation capability at first electrode 116 and an oxygen removal capability at second electrode 118 may be checked. Instead of a setpoint sequence 140, including a constant variable or a variable which is varied in discrete steps 142, setpoint sequences 140 may also include a signal which varies chronologically continuously, in particular a periodic signal, for example, a higher-frequency signal, in particular a higher-frequency oscillation of the Nernst voltage. This may result in oscillations of the pump voltage and the pump current, their ratios also being able to be compared to predefined tolerance bands.

Figure 3:
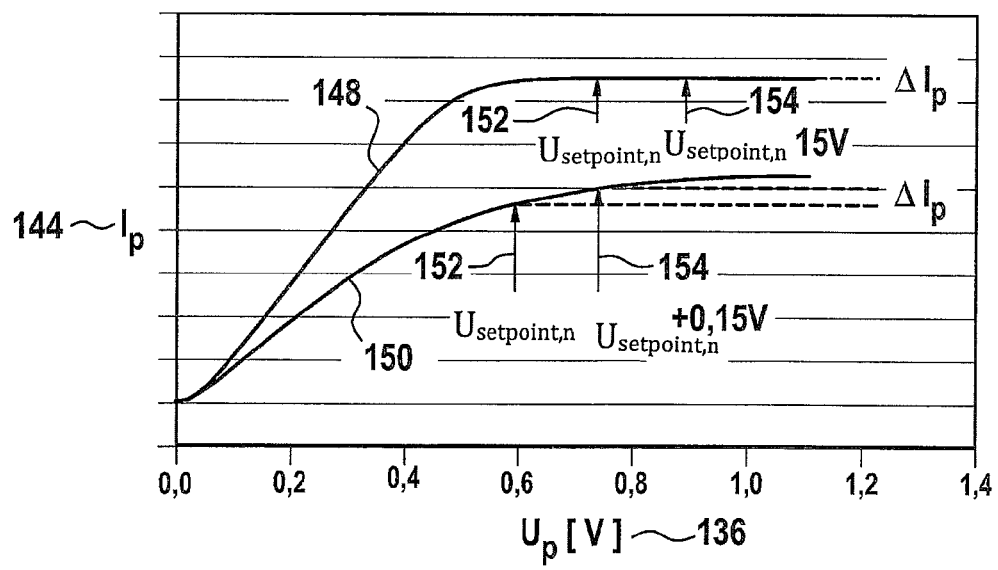
FIG. 3 shows a method according to the present invention having a constant diagnostic signal.

FIG. 3 shows another exemplary embodiment of a method according to the present invention. Sensor elements 114, as are known from the related art, and in particular devices 110, as shown in FIG. 1A and FIG. 1B and described above, may be used to execute this exemplary embodiment. This exemplary embodiment is suited in particular for sensor elements 114 having one cell and sensor elements 114 having two cells. In principle, the method runs as in the above exemplary embodiment, described on the basis of FIGS. 2A, 2B, 2C, 2D. The method may be based on a diagnostic signal 136, in particular on an active variation of a regulating point, in particular a Nernst voltage, in the case of approximately constant operating conditions. Since an aging effect occurs early in the case of high oxygen concentrations, this method may be carried out, for example, in the case of coasting air or during idle speed of a diesel system. In the case of a sensor element 114 having two cells, for example, as shown in FIG. 1A, diagnostic signal 136 may be regulated to a setpoint sequence 140, in particular to a Nernst voltage. Setpoint sequence 140 includes, for example, a regulating point of the Nernst voltage, which deviates, for example, by up to +/−300 mV, which may be by up to +/−200 mV, particularly which may be by up to +/−150 mV from the Nernst voltage during normal operation $U_{setpoint,n}$, for example, 450 mV.

If a sensor element 114 having one cell is used, as shown in FIG. 1B, for example, a diagnostic signal 136 is also applied, diagnostic signal 136, in particular the pump voltage, which need not be regulated to a setpoint sequence 140 in this case. The pump voltage may be varied, for example, by up to +/−300 mV, which may be by up to +/−200 mV, particularly which may be by up to +/−150 mV in relation to the regulating point during normal operation $U_{setpoint,n}$, for example, a Nernst voltage of 450 mV.

Both in the case of sensor elements 114 having one cell and in the case of sensor elements 114 having two cells, the oxygen concentration in cavity 128 may only change slightly due to a variation of setpoint sequence 140, in particular the Nernst voltage, by, for example, up to +/−300 mV, which may be up to +/−200 mV, particularly which may be +/−150 mV, if an activity of the electrodes, in particular first electrode 116 and second electrode 118, is still sufficient. For example, the $O_2$ partial pressure may change by one power of ten per 50 mV Nernst voltage change, i.e., instead of approximately $10^{-9}$ bar (corresponding to 450 mV), for example, approximately $10^{-6}$ bar (corresponding to 300 mV) may be present.

FIG. 3 shows pump current $I_p$, for example, as a response signal 144, as a function of pump voltage $U_p$, for example, as diagnostic signal 136, in volts. Top curve 148 shows a curve of pump current $I_p$ for an intact sensor element 114 and bottom curve 150 shows the curve of pump current $I_p$ for a poisoned sensor element 114.

Top curve 148 and bottom curve 150 have first arrows 152, which each indicate a possible measuring point during a certain setpoint sequence 140 $U_{setpoint,n}$, in particular a constant Nernst voltage as is typical during normal operation. In principle, there may be multiple measuring points. Second arrows 154 identify measuring points during setpoint sequences 140, for example, the Nernst voltage being able to be increased by up to 150 mV to the regulating point during normal operation. Response signal 144, in particular the pump current, has a change $\Delta I_p$, as shown in FIG. 3. A relative change may be compared, for example, to a sensor-typical limiting value.

The relative change of the resulting pump current remains below a sensor-specific limit in the case of an intact sensor element 114, as shown in FIG. 3 in top curve 148. In this case, it is ensured that the characteristic of sensor element 114 is still defined by diffusion barrier 126. A compensation, for example, in the case of coasting air, and an analysis of response signal 144 over a broad measuring range may be possible. Bottom curve 150 shows the curve of the pump current of a contaminated sensor element 114, the relative change of the pump current being greater than a sensor-typical limiting value, in particular greater than a threshold value.

If the threshold value, in particular the sensor-typical limiting value, is exceeded after a comparison, a piece of diagnostic information, in particular an evaluation, may be output, which signals a non-intact sensor element 114. In the case of such a piece of diagnostic information, for example, a valid measuring range of sensor element 114 may be restricted. If the piece of diagnostic information only has negative results at operating points above a certain oxygen concentration, sensor element 114 may thus still be used for sensor signals below this certain oxygen concentration, for example.

What is claimed is:

1. A method for diagnosing a sensor element for detecting at least one fraction of a gas component of a gas in a measuring gas chamber, wherein the sensor element includes at least one first electrode, to which the gas is appliable, and at least one second electrode, and wherein the first electrode and the second electrode are connected via at least one solid electrolyte, the method comprising:
    applying a diagnostic signal between the at least one first electrode and the at least one second electrode, wherein the diagnostic signal is varied according to a pattern that is predefined as a function of passage of a predefined amount of time after each of the applications of the diagnostic signal, so that, after each of a plurality of time intervals following a first application of the diagnostic signal, the diagnostic signal is modified to a respective value that is different than an initial value of the diagnostic signal at the first application; and
    detecting a response signal between the first electrode and the second electrode and that varies according to the value variations of the diagnostic signal.

2. The method of claim 1, wherein the diagnostic signal is selected from a voltage sequence and a current sequence.

3. The method of claim 1, wherein the sensor element includes at least one cavity, to which the gas from the measuring gas chamber may be applied, the first electrode being at least partially connected to the cavity, the cavity being connected to the measuring gas chamber, the second electrode being at least partially connected to the measuring gas chamber.

4. The method of claim 1, wherein the diagnostic signal is regulated to a setpoint sequence between the first electrode and a reference electrode.

5. The method of claim 4, wherein the setpoint sequence includes a variable, which has at least one constant value.

6. The method of claim 4, wherein the setpoint sequence includes a variable, which is chronologically continuously varied.

7. The method of claim 4, wherein the setpoint sequence includes a variable, which is varied in discrete steps.

8. The method of claim 1, wherein the response signal is compared to at least one threshold value as a function of the diagnostic signal.

9. The method of claim 1, wherein the response signal has a relative change, which is compared to a sensor-typical threshold value.

10. The method of claim 1, wherein the sensor element is a sensor element for detecting oxygen in an exhaust gas of an internal combustion engine.

11. The method of claim 1, wherein the sensor element is diagnosed based on a pattern to which values of the response signal, which correspond to the initial value of the diagnostic signal and to each of the values of the diagnostic signal applied after all of the plurality of time intervals, in combination conform.

12. The method of claim 1, wherein the variation of the diagnostic signal is in discrete steps according to a predefined stepped pattern.

13. The method of claim 1, wherein the variation of the diagnostic signal is chronologically continuous.

14. A device for detecting at least one fraction of a gas component of a gas in a measuring gas chamber, comprising:
    at least one sensor element, the sensor element including at least one first electrode, to which the gas may be applied, and at least one second electrode, wherein the first electrode and the second electrode are connected via at least one solid electrolyte; and
    at least one controller configured for diagnosing the sensor element, by performing the following:
    applying a diagnostic signal between the at least one first electrode and the at least one second electrode, wherein the diagnostic signal is varied according to a pattern that is predefined as a function of passage of a predefined amount of time after each of the applications of the diagnostic signal, so that, after each of a plurality of time intervals following a first application of the diagnostic signal, the diagnostic signal is modified to a respective value that is different than an initial value of the diagnostic signal at the first application; and
    detecting a response signal between the first electrode and the second electrode and that varies according to the value variations of the diagnostic signal.

* * * * *